Figure 1:
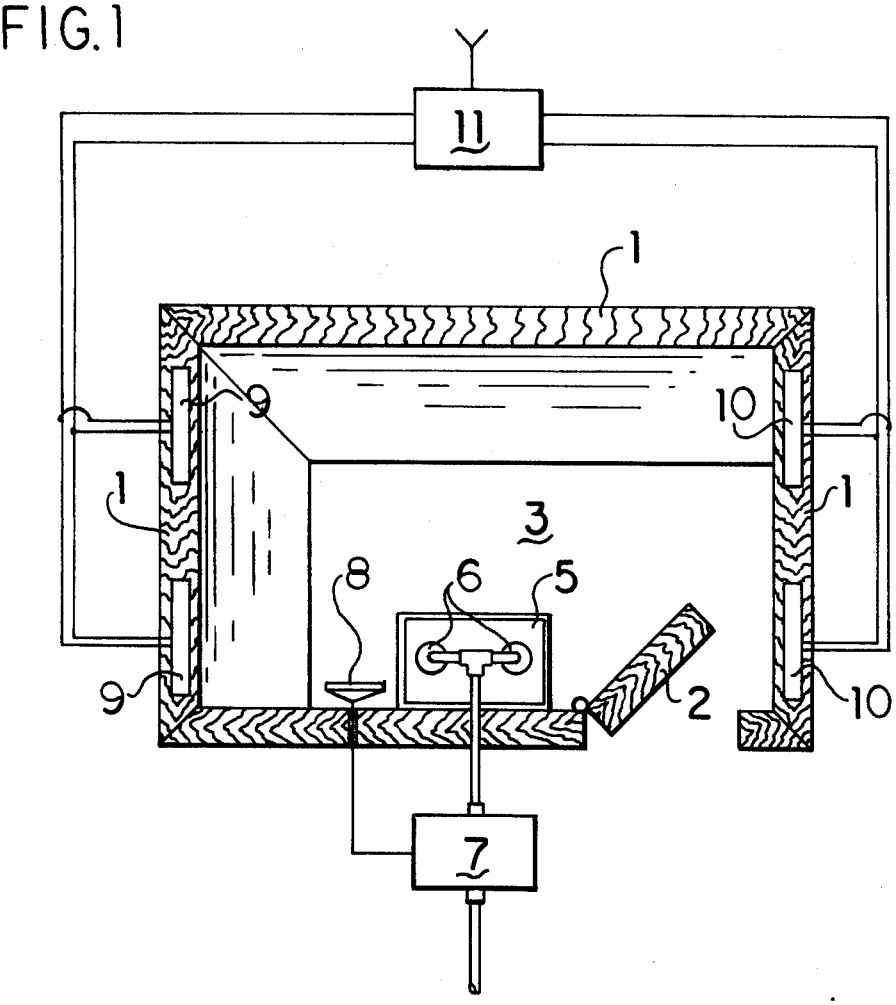

United States Patent [19]
Müller

[11] 4,114,205
[45] Sep. 19, 1978

[54] SAUNA

[76] Inventor: Günter Müller, Bergstrasse 52, Bissendorf 2, Fed. Rep. of Germany, 4501

[21] Appl. No.: 785,269

[22] Filed: Apr. 6, 1977

[30] Foreign Application Priority Data

Apr. 8, 1976 [DE] Fed. Rep. of Germany ....... 2615294

[51] Int. Cl.² ............................................. A61H 33/06
[52] U.S. Cl. ............................................ 4/160; 128/371
[58] Field of Search .................................... 4/160–164; 128/367, 371, 190, 192

[56] References Cited

U.S. PATENT DOCUMENTS

| 2,184,644 | 12/1939 | Homberger | 128/371 |
| 3,467,813 | 9/1969 | Raabe | 4/160 X |
| 3,483,672 | 12/1969 | Jahnke | 128/190 |
| 3,678,337 | 7/1972 | Grauvogel | 128/190 X |
| 3,680,281 | 8/1972 | Jahnke | 128/190 X |
| 3,739,144 | 6/1973 | Janson | 4/160 X |

FOREIGN PATENT DOCUMENTS

336 of 1901 United Kingdom ..................... 128/371

Primary Examiner—Stuart S. Levy
Attorney, Agent, or Firm—Allison C. Collard

[57] ABSTRACT

A suana includes a wooden housing, having a closable entryway and a heating device and a humidifier, each of which is disposed in the housing, and includes a control element for respectively regulating the temperature and humidity in the housing. At least one pair of space-apart electrodes are disposed opposite one another in said housing for creating an electric field within the inner space of the housing, and at least one irradiation lamp is also disposed in the housing for creating light within the total visible spectrum of light, including UV and IR irradiation.

4 Claims, 2 Drawing Figures

SAUNA

The invention relates to a sauna. More particularly, it relates to a sauna which includes a wooden housing, having a closable entryway and a heating device, which is controlled by a temperature control element.

Saunas, such as the so-called "Finnish" sauna, are of course well known in the art. The "Finnish" sauna operates with very hot and dry air, typically at a relative humidity of about 10% and temperature of over 100° C. Consequently, the body of the person taking the bath is exposed to very high temperatures, and is cooled down by perspiration and the evaporation of the perspiration. This naturally induces excessive stress on the circulatory system of the person taking the bath. In order to maintain a minimum of air moisture in the "Finnish" sauna, water is applied to the heating device, which immediately evaporates and creates a sudden evaporation cloud. This, in turn, results in a sudden increase of heat stress for the body of the person taking the bath. As a result, the "Finnish" sauna is not usable for a number of therapeutic purposes and, in particular, for people having a weakened circulatory system. Also well known in the art is the so-called "steam bath". In such a bath, the bathing person is exposed to an atmosphere which is saturated to 100% and very often supersaturated with water vapor. Under these conditions, the body is unable to evaporate the perspiration secreted from the body, as a result of which the heat stress on the body is even more severe than in the drier "Finnish" sauna. For this reason, considerably lower temperatures may be employed in the steam bath. However, even if the steam baths are employed at lower temperatures, the danger of a heat build-up in the body still exists, so that people who have a week circulatory system are endangered.

The physiological effects of the various types of climatic conditions are well known in physiotherapy. In particular, the following climatic factors have a very intensive therapeutic effect: air temperature, air moisture, sun rays, electrical conductivity of air, presence and intensity of electric fields. Control of these climatic factors have been used for a long time in physiotherapy.

Accordingly, it is an object of the present invention to provide an improved sauna of the aforementioned type which prevents an excessive heat stress on the body of the person taking the bath, and which provides certain climatic controls which may be adjusted to provide a desired therapeutic effect.

In accordance with the objects of the invention, a sauna is provided which essentially includes a wooden housing having a closable entryway, a heating device which is controlled by a temperature control element, and a humidifier disposed within the wooden housing and controlled by a humidifier regulator. In or on the walls and/or floor, or ceiling of the wooden housing, electrodes are oppositely arranged with respect to each other, for creating an electric field within the inside of the housing. In or on the ceiling of the wooden housing, one or a plurality of irradiation lamps are provided to create light within the total visible spectrum, including UV and IR irradiation.

The sauna, in accordance with the invention, permits adjustment of the air moisture and air temperature to values which are not dangerous to the circulatory system of the person and to the therapy applied, for example, a temperature of 35°–36° C., and an air moisture content of about 60 to 70%. In addition, an electrical field may be created in the inner space of the sauna, by means of the electrodes, which in its intensity and frequency corresponds to the electrical fields which are present in certain stimulation climatic zones. By means of the irradiation lamps, irradiation conditions may be created in the inner space of the sauna as are present in certain climatic zones, due to natural sun rays. The irradiation, particularly in the UV-range, in cooperation with the electrical field, provides a part ionization of the air in the sauna, so that the same becomes electrically conductive, as is the case in certain therapeutically-effective stimulant climatic zones. Hence, it can be said that in the sauna, in accordance with the invention, any desired climatic factor may be created. Therefore, the sauna, in accordance with the invention, may be used for different desired therapeutic purposes.

In a preferred embodiment of the invention, filters in all spectral colors are mounted on the irradiation lamps. The filters are made of glass or plastic discs bearing a spectral color and are moveable in front of the lamps by means of tracks. As a result, it is possible to provide the desired irradiation condition, without exchanging the individual irradiation lamps. If, for example, irradiation effects are to be created as they prevail in the shadow of a tree, the corresponding filters are displaced in front of the irradiation lamps, which filters out the wave lengths which are not present in the shadow of a tree. The humidifier used in the sauna, in accordance with the invention, is essentially provided with one or a plurality of water jet nozzles, which are provided above the heating device, whereby the supplied water is sprayed in very fine droplets above the heating device. This type of air humidification prevents a raining down of the introduced air moisture, because the water droplets evaporate at least when reaching the heating device. At the same time, the formation of a steam cloud is prevented which always occurs in a "Finnish" sauna, when water is applied to the heating device.

Preferably, a control element is provided for the electrodes, which supplies to the electrodes a right-angle voltage impulse with a frequency of 1 to 10 Hertz. Such a control system and the frequency stated, allow the best possible simulation of electrical fields being present in the natural climate.

Most desirably, the electrodes are built into the wall panels of the wooden housing. However, they may also be suspended on the walls.

Other objects and features of the present invention will become apparent from the following detailed description when taken in connection with the accompanying drawing, which disclose several embodiments of the invention. It is to be understood that the drawing is designed for the purposes of illustration only, and is not intended as a definition of the limits and scope of the invention disclosed.

Figure 2:
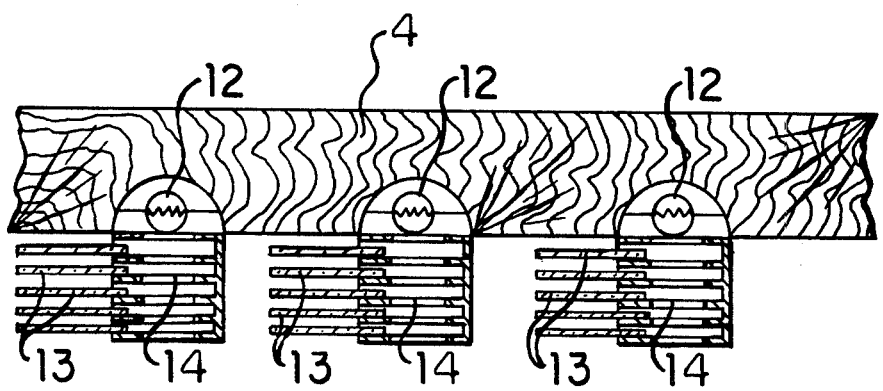

In the drawing, wherein similar reference numerals denote similar elements throughout the several views:

FIG. 1 is a schematic plan view of a sauna, embodying the present invention, with the ceiling removed to show internal construction; and FIG. 2 is a schematic, vertical sectional view through the irradiation lamps, which are mounted on the ceiling of the sauna.

Referring to FIG. 1, therein illustrated is a sauna embodying the present invention and including vertical walls 1 and an entrance door 2. Walls 1 are connected with a floor 3. The space which is formed by walls 1 and floor 3, is closed off with a ceiling 4 (see FIG. 2). The ceiling is not shown in FIG. 1. All walls 1, floor 3 and ceiling 4 consist of heat-insulated, wooden panels.

An electric heating device 5 is provided in the inner space of the sauna, which is connected in a known manner with a temperature regulator, so that the heat within the sauna may be adjusted to a defined or desired temperature. Two water jet nozzles 6 are mounted above heating device 5, with the water being sprayed in fine droplets from the nozzles onto the heating device 5. The water supply to water jet nozzles 6 is so controlled by a control unit 7, responsively or dependently coupled to a hygrometer 8 in the inner space of the sauna, so that a constant humidity is maintained in the sauna.

Electrodes 9 and 10 are provided in two oppositely-arranged walls 1 of the sauna, which are connected to a control device 11, which also serves as the power supply, in such a manner that an electric field is generated in the inner space of the sauna between electrodes 9 and 10. The control device 11 generates right-angular voltage impulses or rectangular pulsed waves with an adjustable frequency between 1 and 10 Hertz. If need be, the electrodes 9, 10 may be oppositely arranged in the floor 3 and ceiling 4.

As shown in FIG. 2, a plurality of irradiation lamps 12 are provided in ceiling 4 of the sauna, which radiate light in the visible spectrum, and also in the IR and UV range. A plurality of glass or plastic discs form optical filters 13 beneath irradiation lamps 12. Filters 13 are displaceably mounted in tracks 14, so that they may be selectively arranged in front of lamps 12. Filters 13 contain one spectral color each, so that each filter 13 only filters a defined light wave length from the radiation light of the irradiation lamps. By disposing filters 13 totally, or partly, in front of irradiation lamps 12, various irradiation conditions i.e., irradiation with light of a predetermined frequency or frequencies may be generated. Irradiation lamps 12 simultaneously serve as lights for the inner space of the sauna.

While only one embodiment of the present invention has been shown and described, it will be obvious to those persons of ordinary skill in the art, that many changes and modifications may be made thereunto without departing from the spirit and scope of the invention.

What is claimed is:

1. A sauna comprising:
   a wooden housing, having a floor, a ceiling, upstanding sidewalls joining said floor and ceiling, and a closable entryway;
   a heating device disposed in said housing and including a temperature control element for regulating the heat emitted by said heating device at a temperature of approximately 35° C.,
   a humidifier including at least one water jet nozzle, which is disposed above said heating device, to spray water in fine droplets above said heating device disposed in said housing and including a humidity control element for regulating the water vapor produced by said humidifier at an air moisture content of approximately 60 to 70 percent;
   at least one pair of spaced-apart electrodes, disposed opposite one another in said housing, for creating an electric field within the inner space of said housing;
   at least one irradiation lamp, disposed in said housing for creating light within the total visible spectrum of light, and UV and IR irradiation; and
   a plurality of filters in all spectral colors, disposed adjacent said irradiation lamp, each of which comprises a glass or plastic disc bearing a different spectral color, said filters being slidably mounted on tracks so as to be displaceable in front of said irradiation lamp.

2. The sauna according to claim 1, additionally including a control element for said electrodes, which supplies rectangular pulsed waves to said electrodes with a frequency of 1 to 10 Hertz.

3. The sauna according to claim 1, wherein said housing has two, space-apart, opposing sidewalls and wherein one of said pair of electrodes is mounted in or on one of said sidewalls, and the other of said electrodes is mounted in or on the other of said sidewalls.

4. The sauna according to claim 1, wherein said irradiation lamp is mounted in or on said ceiling.

* * * * *